United States Patent [19]

Chen et al.

[11] Patent Number: 5,837,799
[45] Date of Patent: Nov. 17, 1998

[54] FIRE-RETARDANT COMPOUND, A PROCESS FOR PRODUCING SAID FIRE-RETARDANT COMPOUND AND A FIRE-RETARDED THERMOPLASTIC RESIN COMPOSITION INCLUDING SAID FIRE-RETARDANT COMPOUND

[75] Inventors: Toshihiko Chen; Yoshiaki Nakamura; Tetsunori Sato; Yoshiyuki Morikawa, all of Tokyo, Japan

[73] Assignee: Tohto Kasei Co., Inc., Tokyo, Japan

[21] Appl. No.: 697,457

[22] Filed: Aug. 23, 1996

[30] Foreign Application Priority Data

Aug. 25, 1995 [JP] Japan .................................... 7-217664

[51] Int. Cl.$^6$ .................................................. C08G 59/00
[52] U.S. Cl. .................. 528/102; 528/103; 528/104; 524/114; 524/373; 524/374; 525/107; 525/109; 525/115; 525/423; 525/430; 525/438; 525/442; 525/449; 525/396; 525/463; 525/522; 525/534
[58] Field of Search ..................... 528/102, 103, 528/104; 525/107, 109, 115, 423, 430, 438, 442, 449, 463, 396, 522, 534; 524/114, 373, 374

[56] References Cited

U.S. PATENT DOCUMENTS

| | | | |
|---|---|---|---|
| 4,567,242 | 1/1986 | Nishibori et al. | 525/535 |
| 4,994,515 | 2/1991 | Washiyama et al. | 524/269 |
| 5,250,590 | 10/1993 | Nakai et al. | 525/463 |
| 5,281,639 | 1/1994 | Satoh et al. | 524/114 |
| 5,376,718 | 12/1994 | Yada | 525/523 |

FOREIGN PATENT DOCUMENTS

| | | |
|---|---|---|
| 62-004737 | 1/1987 | Japan . |
| 5-93120 | 4/1993 | Japan . |
| 5-239269 | 9/1993 | Japan . |
| 6-299007 | 10/1994 | Japan . |
| 06306162 | 11/1994 | Japan . |

*Primary Examiner*—Randy Gulakowski
*Attorney, Agent, or Firm*—Sherman and Shalloway

[57] ABSTRACT

A fire-retardant compound including bromine indicated by general formula (1), wherein the end group X and Y are comprised by A or B shown in formula (2), and the said fire-retardant compound is a mixture of the composition including 15 to 30% of X=Y=A, the composition including 40 to 60% of X=A and Y=B and the composition including 20 to 35% of X=Y=B, and degree of polymerization n is indicated by an integral number from 0 to 30, and a flame-retarded thermoplastic resin including said fire-retardant compound.

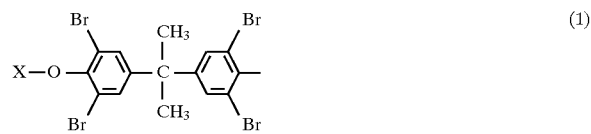

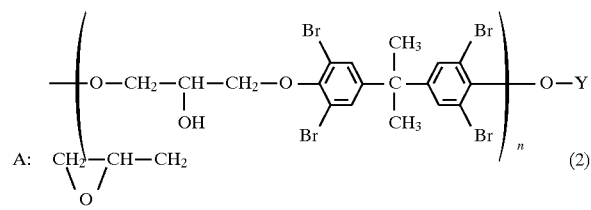

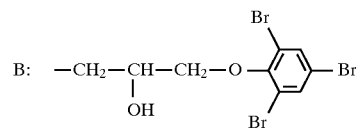

8 Claims, No Drawings

FIRE-RETARDANT COMPOUND, A PROCESS FOR PRODUCING SAID FIRE-RETARDANT COMPOUND AND A FIRE-RETARDED THERMOPLASTIC RESIN COMPOSITION INCLUDING SAID FIRE-RETARDANT COMPOUND

BACKGROUND OF THE INVENTION

This invention relates to a fire-retardant compound to be added to thermoplastic resin, a process for producing it and a resin composition including said fire retardant compound.

DESCRIPTION OF THE PRIOR ART

The specific kinds of styrene resin such as high impact polystyrene (HIPS), ABS and the like have an excellent mechanical property and is superior in electrical insulation and moldability. And, engineering plastics such as PET, PBT and the like are improved to possesses additional specific properties e.g. heat resistance and dimensional stability. Therefore, recently these engineering plastics have been widely applied for OA devices, housing of household electric appliances, automotive parts and the like. However, since these resins are inflammable substance, from a viewpoint of security, the improvement to provide a flame retardant property to these resins is becoming very impatient requirement.

Further, in the field of OA devices, household electric appliances and the like, these resins are usually used indoors, however, have a tendency to become yellow by the influence of light from fluorescent lamp or daylight from outdoor with the passage of time. And accordingly, the improvement in light resistance is also becoming important.

Various kinds of organic compound substituted by halogen have been proposed as the additives which provide a property of fire resistance to thermoplastic resin represented by styrene resin. As the said fire-retardant compound, comparative low molecular weights organic compounds including bromine such as tetrabromo bisphenol A (TBA) or poly(bromo diphenyl ether) (PBDPE) are mentioned. However, though low molecular-weight fire-retardant compound have a merit in cost for manufacturing, but have problems in bleed-out, deterioration in heat resistance, light resistance and stability against heat. Therefore, recently, higher molecular-weight oligomer type ones that molecular design is possible is come to be used. As the examples of said compound, brominated epoxy of which two end groups are epoxy group (YDB-406, 408 of Tohto Kasei, and the like which are dealt on the market), modified brominated epoxy of which two end groups are capped by tribromo phenol (TB-60, 62 of Tohto Kasei, and the like which are dealt on the market), bromo polycarbonate oligomer, and the like.

In Japanese Laid-open Patent Publication 1-287132, it is disclosed that styrene resin composition which is superior in impact resistance and has light resistance and high fire resistance is obtained by adding compound including halogen which has epoxy groups in both end groups to ABS resin. However, it has a defect in adhesive property (non-stickiness) to metal.

Further, in Japanese Laid-open Patent Publication 5-117463, it is proposed that fire-retardant agent which is superior in releaseability of product from a mold is obtained by adding halogenated epoxy fire-retardant compound including long chain aliphatic carboxylic acid compound to styrene resin. However, since by including long chain aliphatic carboxylic acid compound, heat stability and fire-retard-efficiency of resin composition are dropped, in fact, it was difficult to obtain fire-retarded styrene resin composition which has excellent quality balance.

Further, in Japanese Laid-open Patent Publication 62-4737 and 63-73749, it is suggested to use as fire-retardant compound mixture of halogenated epoxy modified, more than 60% of both of which two terminal epoxy groups are capped with TBP (tribromo phenol), and halogenated epoxy resin including smaller than 40% epoxy groups, but this method has a defect in light resistance. In Japanese Laid-open Patent Publication 1-170630, it is proposed to use as fire-retardant compound modified brominated low molecular-weight compound, 50% of both or one of which two ends are capped with TBP, but it has a defect that heat resistance is inferior for low molecular weight and light resistance is inferior.

As above mentioned, although the brominated epoxy oligomer and modified brominated epoxy oligomer of which amount of use are increased recently have many excellent features, particularly in light resistance, they have defects as follow, and are desired to be improved.

Namely, if the brominated epoxy oligomer is added to thermo plastic resin, during kneading and molding process with extruder or injection molding machine the said oligomer adheres to the screw of these molding machines. And after continuous production, because the adhered oligomer is exposed to high temperature for long time, it is tarnished and degraded. These tarnished and degraded substance are contaminated as foreign matter in compound and in a molded product.

On the other hand, modified brominated epoxy oligomer does not have adhesive property to metal as brominated epoxy has, however, since the ends are capped with tribromo phenol, it is inferior in light resistance and tends to turn to yellow.

SUMMARY OF THE INVENTION

The inventors have conducted various studies to obtain fire-retardant agent having light resistance which said brominated epoxy oligomer has and non-adhesive property to metal which said modified brominated epoxy oligomer has, and accomplished the present invention. A primary object of the present invention is to provide a new fire-retardant compound having light resistance and non-adhesive property to metal, and a resin composition including said fire-retardant compound.

An important point of the present invention is a fire retardant compound including bromine indicated by general formula (1), wherein the end group X and Y are comprised by A or B indicated in formula (2), and the said fire-retardant compound is a mixture of the composition including 15 to 30% of X=Y=A, the composition including 40 to 60% of X=A and Y=B and the composition including 20 to 35% of X=Y=B, and degree of polymerization n is indicated by an integral number from 0 to 30.

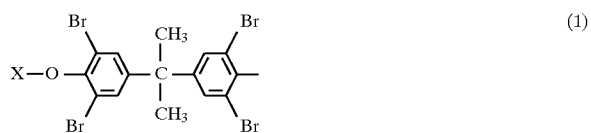
(1)

-continued

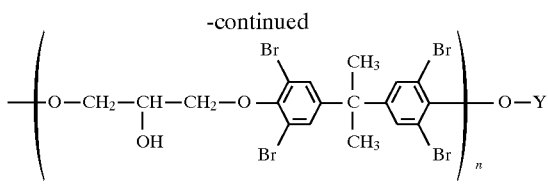

In this case, A and B are indicated as follows.

A: 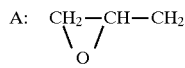 (2)

B: 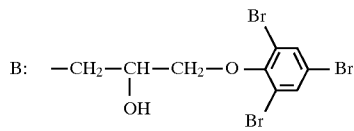

DETAILED DESCRIPTION OF THE INVENTION

The present invention is explained more particularly as follows.

There ate several methods to obtain the new fire retardant agent of Formula (1) in this invention. Specifically, the most representative method is to obtain (1) consisted with end groups A and B by reacting tetrabromo bisphenol A (TBA) and mixture of epichlorohydrine (ECH), tribromo phenol (TBP) and methyl isobutyl ketone (MIBK) in the presence of alkali metal hydroxide. In this method, degree of polymerization n can be controlled with molar ratio of TBA and ECH, and ratio of end group A and B can be controlled with molar ratio of ECH and TBP. Or, after obtaining (1) with end group A, it is possible to produce by reacting TBP and end group A.

The second method is to use tribromo phenol glycidyl ether (TBPGE), that is, the method for obtaining the new fire retardant agent by charging fixed quantity of TBPGE and ECH with MIBK solvent and reacting in the presence of alkali metal hydroxide. Similarly to the first method, in this method, degree of polimerization n can be controlled with molar ratio of TBA and (ECH+TBPGE), and ratio of end group A and B can be controlled with molar ratio of ECH and TBPGE. Or, it is possible to add ECH after reacting TBA and TBPGE.

The third method is to react tetrabromo bisphenol A type epoxy resin wherein epoxy equivalent is 350 to 700 g/eq, softening point is 50° to 105° C. and bromine content is 50 to 53%, TBA and TBP in the presence of catalyst to obtain the fire retardant agent of formula (1).

Desirably, for tetrabromo bisphenol A type epoxy resin used in this method, epoxy equivalent is 350 to 700 g/eq and more desirably 380 to 420, softening point is 64° to 74° C., and bromine content is 46 to 50%. It is difficult to treat diglycidyl ether of tetrabromo bisphenol A having lower epoxy equivalent than that because it is crystalloid or apt to crystallize, and it is uneconomical for high producting cost. On the other hand, it is undesirable to treat one of higher epoxy equivalent than that because of the lack of degree of freedom in molecular design. For the said epoxy resin, epoxy resin obtained by direct reaction of TBA and ECH is desirable because color feature is favorable and there is no catalyst remaining difference. However, it is possible to use that obtained by addition reaction of low molecular-weight epoxy resin and TBA according to used catalyst, too. In this method, considering degree of polimerization n of raw material epoxy, n can be controlled by controling molar ratio of epoxy group and phenolic hydroxyl group of TBA. The ratio of end group A and B can be calculated as the first epoxy group—hydroxyl group of TBA—hydroxyl group of TBP (B) A, molar number of charged TBP=B.

In the reaction of tribromo phenol and epoxy group, reaction velocity is slow for steric hindrance of bromine atom existing at ortho position to hydroxyl group of tribromo phenol, using of catalyst is desirable. As the catalyst, conventionally public known alkaline metal salt such as caustic alkali, caustic kalium and so on, tertiary amine such as tributyl amine, triethyl amine and so on, and quarternary ammonium salt such as tetrabutyl ammonium bromide can be used, too. However, in the case of alkaline catalyst, reaction velocity is slow and such impediment as hydrolysis is apt to occur arises in being used as fire retardant agent of polyester and polycarbonate. Amine catalyst has a defect that products are colored extremely and it is not suited to be used for white products, namely, products are inferior in light resistance. For enforcement of the invention, considering about reaction velocity, color feature of products, heat stability, and so on, following catalysts can be mentioned as desirable catalyst, that is, phosphine such as triphenyl phosphine, phosphate catalyst such as ethyl triphenyl phosphonium iodide, ethyl triphosphonium bromide, ethyl triphenyl phosphonium acetate and n-butyl triphenyl phosphonium bromide. For these catalysts, using in 200 to 5,000 ppm to phenol element of reactants, more desirably 400 to 3000 ppm, is desirable.

The fourth method is to react tetrabromo bisphenol A type epoxy resin wherein epoxy equivalent is from 600 to 1300 g/eq, softening point is 95° to 140° C. and bromine content is 50 to 53% and tribromo phenol in the presence of catalyst to obtain the fire retardant agent of formula (1).

Tetrabromo bisphenol A type epoxy resin used in this method is obtained by direct reaction of TBA and ECH, and desirably, epoxy equivalent is 600 to 1300 g/eq and more desirably 600 to 770 g/eq, softening point is 95° to 115° C., and bromine content is 50 to 52%. The fire retardant agent of formula (1) obtained by adding objective amount of TBP to epoxy resin having epoxy equivalent about this has proper number of n and wide utility. This method desires phosphate catalyst as reaction catalyst, too.

The fifth method is to react tetrabromo bisphenol A type epoxy resin wherein epoxy equivalent is 350 to 700 g/eq, softening point is 50° to 105° C. and bromine content is 46 to 52%, tribromophenol A and tribromo phenyl glycidyl ether in the presence of catalyst to obtain the new fire retardant agent. This method is similar to the third method except for using TBPGE instead of TBP. In this method, TBA and TBPGE are reacted at first, and secondly epoxy resin are reacted. Otherwise, unreacted TBPGE remains and causes defects such as falling down of softening point or generation of gaseous products.

Formula (1) is oligomer, and the molecular weights are distributed. The mean degree of polymerization n is from 0 to 30, and should be selected to obtain the best property for each resin to which the oligomer is added. In general, it is preferable to choose degree of polymerization n=0 to 5 for styrene resin, and degree of polymerization n=3 to 30 for PET, PBT.

The end group A of Formula (1) is introduced to keep light resistance which is a good point of brominated epoxy oligomer, and to improve the defect of adhering to metal the end group B is introduced. In the case of the fire-retardant compound of this invention, the mixture of the oligomer must include 15 to 30% of X=Y≐A and 40 to 60% of X=A and Y=B for expected effect of light resistance. The mixture of the oligomer must include 20 to 35% of X=Y=B and 40 to 60% of X=A and Y=B for expectation of improvement of adhering to metal.

As the examples of thermoplastic resin to which the fire-retardant compound of this invention to be added, following resins can be mentioned. That is, polystyrene resin, polyester resin such as poly(ethylene terephthalate) and poly(buthylene terephthalate), polyolefin resin e.g. polypropylene, polyamide resin e.g. nylon, polycarbonate resin, polyacetal (POM) resin, polyarylate (PAR) resin, polyether resin e.g. modified polyphenylene (PPO) resin, and the like.

In the actual use of the fire-retardant compound of the present invention to be combined with thermoplastic resin, the preferable amount of it is 1 to 30 parts by weight of the resin, and is more preferable amount is 5 to 25 parts. The fire-retardant compound of the present invention can be used together with other fire-retardant compounds as long as the effects of the invention are kept. Further, as occasion demands, using together of fire-retardant auxiliaries such as antimony trioxide, antimony pentaoxide and molybdenum oxide, lubricant, ultraviolet absorbent, antioxidant, coloring pigment, dye, release agent, filler, and other additives are not specifically limited.

EXAMPLES

The present invention will now be described in more detail with the Examples and Comparative Examples, but is not limited to the Examples. The indications of part and % in the examples are given on the basis of weight. And in this invention, the following method of test were used.

(1) epoxy equivalent: JIS K-7234

(2) softening point: JIS K-7236

(3) light resistance ΔE: Using Sunshine Weather Meter, color difference of test specimen were measured with colour-difference meter (Tokyo Denshoku) before and after 62±2° C.×48 hours weathering test (without rain).

(4) flammability test: Measured according to UL-94.

(5) adhesive property to metal: The first roll of 6 inch metallic heat roll was set at 200° C., the second was set at 60° C. After test specimen were pressed lightly to the first roll for 3 minutes and then kneaded for 3 minutes, kneaded resin was removed, and the condition of adhesion to the roll was observed.

Evaluation a: no adhering to roll b: removed from roll easily c: adhered to the roll and hard to remove (6) composition of end group: Using liquid chromatography (LC) with tetrahydrofuran (THF)/water($H_2O$)/acetonitrile (ACN) for moving bed, and TSKgelODS-120T (Toso) for column, measured with UV-detector at 280 nm, and shown with mean values of ratio of area of each peaks.

Example 1

In a 3-liter separable flask with a thermometer, a stirrer, a dropper, and a condenser, 544 g of TBA, 138.8 g of ECH and 210 g of methyl isobutyl ketone (MIBK) were charged, heated to dissolve with nitrogen purge, 37.5 g of 48 wt. % aqueous sodium hydroxide solution was dropped in over 30 minutes at 95° C. After reaction for 4 hours, the resulting solution was weakened with 160 g of TBP and 55 g of MIBK, 150 g of 48 wt. % aqueous sodium hydroxide solution was dropped in over 30 minutes, and then reacted for 12 hours, 530 g of MIBK and 320 g of water were added, and then allowed to stand and water layers were separated to remove the generated salt. Further, after the solution was washed with same amount of water 5 times and filtered, solvent was recovered at 150° C. under vacuum of 5 Torr to obtain the objective fire-retardant compound A. The physical properties of A are shown in Table 1.

Example 2

In a 1-liter separable flask, 800 g of EPOTOHTO YDB-400 (Tohto Kasei, epoxy equivalent: 400 g/equivalent, softening point: 67° C., bromine content: 49 wt. %), 136 g of TBA, 224 g of TBP and 0.25 g of triphenyl phosphine (TPP) were charged, reacted at 160° C. for 5 hours with nitrogen purge to obtain the objected fire-retardant compound B. The physical properties of B are shown in Table 1.

Example 3

Using the same procedure as in Example 2 except that 237 g of TBP was used, fire-retardant compound C was obtained. The physical properties of C are shown in Table 1.

Reference Example 1

Reaction was carried out similarly to Example 2 except that 137 g of TBP was used. The physical properties of the obtained fire-retardant compound D are shown in Table 1.

Reference Example 2

Reaction was carried out similarly to Example 2 except that 347 g of TBP was used. The physical properties of the obtained fire-retardant compound E are shown in Table 1.

In addition, as the comparison, the physical properties of YDB-406 (Tohto Kasei) as the example of brominated epoxy oligomer and that of TB-62 (Tohto Kasei) as the example of modified brominated epoxy oligomer are shown in Table 1.

TABLE 1

|  | Ex. 1 | Ex. 2 | Ex. 3 | Ref. 1 | Ref. 2 | Ref. 3 | Ref. 4 |
|---|---|---|---|---|---|---|---|
| Fire retardant agent | A | B | C | D | E | YDB-406 | TB-62 |
| content of X = Y = A | 20.4 | 26.8 | 17.3 | 42.2 | 7.5 | 100 | 1.3 |
| content of X = A, Y = B | 48.8 | 46.9 | 48.5 | 44.7 | 41.0 | 0 | 5.2 |
| content of X = Y = B | 30.8 | 26.3 | 34.2 | 13.1 | 51.5 | 0 | 93.5 |
| bromine content % | 55.2 | 54.6 | 55.4 | 53.2 | 56.3 | 50.5 | 58.2 |
| softening point °C. | 110 | 108 | 112 | 105 | 114 | 102 | 117 |

Example 4

In the same apparatus as Example 1, 544 g of TEA, 97.1 g of ECH, 177.8 g of tribromo phenyl glycidyl ether (TBPGE) of which epoxy equivalent is 395 g/eq and bromine content is 60.8%, and 205 g of MIBK were charged, heated to dissolve with nitrogen purge, 87.5 g of 48 wt. % aqueous sodium hydroxide solution was dropped in over 90 minutes at 95° C. After reaction for 2 hours, 350 g of MIBK and 230 g of water were added, and then allowed to stand and water layers were separated to remove the generated salt. Further, after the solution was washed with same amount of water 5 times and filtered, sovlent was recovered at 150° C. under vacuum of 5 Torr to obtain the objective fire-retardant compound F. The physical properties of F are shown in Table 2.

Example 5

IN a 1-liter separable flask, 1440 g of EPOTOHTO YDB-408 (Tohto Kasei, epoxy equivalent:720 g/eq, softening point: 110° C., bromine content:51 wt. %), 331 g of TBP, and 0.33 g of ethyl triphenyl iodide as the catalyst were charged, reacted at 130° C. for 1 hour and at 160° C. for 5 hours with nitrogen purge to obtain the objected fire-retardant compound G. The physical properties of G are shown in Table 2.

Example 6

In a 3-liter separable flask with a reflux condenser, 816 g of TBA, 592.5 g of tribromo phenyl glycidyl ether (TBPGE) of which epoxy equivalent is 395 g/eq and bromine content is 60.8%, 600 g of methyl isobutyl ketone and 0.8 g of TPP were charged and reacted at reflux temperature for 2 hours. And then, 1200 g of EPOTOHTO YDB-400 (Tohto Kasei, epoxy equivalent:400 g/eq, softening point:67° C., bromine content:49 wt. %) were added, and reacted at 170° C. for 5 hours removing solvent MIBK by distillation to obtain the objected fire-retardant compound H. The physical properties of H are shown in Table 2.

Reference Example 5

Using the same procedure as in Example 2 except that 1.08 g of tributylamine instead of triphenyl phosphine was used to obtain the fire-retardant compound I. The physical properties of I are shown in Table 2.

TABLE 2

|  | Ex. 4 | Ex. 5 | Ex. 6 | Ref. 5 |
|---|---|---|---|---|
| Fire retardant agent | F | G | H | I |
| content of X = Y = A | 25.0 | 24.8 | 29.8 | 26.3 |
| content of X = A, Y = B | 47.1 | 52.1 | 49.9 | 45.8 |
| content of X = Y = B | 27.9 | 23.8 | 20.3 | 27.9 |
| bromine content % | 54.1 | 55.0 | 53.4 | 54.5 |
| softening point °C. | 106 | 118 | 109 | 109 |

Examples 7 to 9 and Comparative Examples 1 to 4

Secondly, in order to examine the effect of obtained fire-retardant compound, the physical properties of compound which is combined with thermoplastic resin was measured. That is, adding fire-retardant compound A to C obtained in Examples 1 to 3 for Examples 7 to 9, and fire-retardant compound D to E of Reference Examples 1 to 2, YDB-406 and TB-62 (mentioned above) for Comparative Examples 1 to 4, for comparison, to resin in ratios shown in Table 3 respectively, they were mixed with Henschel mixer, kneaded by a biaxial extruder (Ikegai Tekko, PCM-30) to obtain compounds. And test specimen were made of the obtained compounds by injection molding. Using the test specimen, flammability, adhesive property, and light resistance were measured. The results are shown in Table 3.

TABLE 3

|  | Ex. 7 | Ex. 8 | Ex. 9 | Com. 1 | Com. 2 | Com. 3 | Com. 4 |
|---|---|---|---|---|---|---|---|
| ratio |  |  |  |  |  |  |  |
| ABS resin | 74 | 74 | 74 | 73 | 74 | 72 | 75 |
| Fire retardant agent | A | B | C | D | E | YDB-406 | TB-62 |
|  | 20 | 20 | 20 | 21 | 20 | 22 | 19 |
| $Sb_2O_3$ | 4 | 4 | 4 | 4 | 4 | 4 | 4 |
| $TiO_2$ | 2 | 2 | 2 | 2 | 2 | 2 | 2 |
| flammability UL-94 | V-0 | V-0 | V-0 | V-0 | V-0 | V-0 | V-0 |
| light resistance ΔE | 2.3 | 2.4 | 2.5 | 2.1 | 3.2 | 1.6 | 3.5 |
| adhesive property to metal | a | a | a | c | a | c | a |

Examples 10 to 12 and Comparative Example 5

Similarly to Examples 7 to 9, adding fire-retardant compound F to H obtained in Examples 4 to 6 for Examples 10 to 12 and fire-retardant compound I of Reference Example for Comparative Example 5 to resin in ratios shown in Table 4 respectively, they were mixed with Henschel mixer, kneaded by a biaxial extruder (Ikegai Tekko, PCM-30) to obtain compounds. And test specimen were made of the obtained compounds by injection molding. Using the test specimen, flammability, adhesive property, and light resistance were measured. The results are shown in Table 4.

TABLE 4

|  | Ex. 10 | Ex. 11 | Ex. 12 | Com. 5 |
|---|---|---|---|---|
| ratio |  |  |  |  |
| ABS resin | 74 | 74 | 73 | 74 |
| Fire retardant agent | F | G | H | I |
|  | 20 | 20 | 21 | 20 |
| $Sb_2O_3$ | 4 | 4 | 4 | 4 |
| $TiO_2$ | 2 | 2 | 2 | 2 |
| flammability UL-94 | V-0 | V-0 | V-0 | V-0 |
| light resistance ΔE | 2.4 | 2.3 | 2.2 | 3.1 |
| adhesive property to metal | a | a | a | a |

As can be seen clearly from Table 3 and Table 4, the fire retardant agent of the present invention exhibits excellent effect that it can keep light resistance and improve adhesive property to metal without decrease of content of bromine although it is brominated epoxy oligomer type. Accordingly, resin composition to which the fire retardant agent is added is highly flame-retarded and superior in light resistance, heat resistance and flowability, and has property improved not to adhere to metallic part of screw of injection molding machine and extruder, cylinder, and mold. In result, it can provide thermoplastic resin composition to use in the field in which flame resistance is required such as OA devices, housing of household electric appliances, automotive parts, and the like.

What is claimed is:

1. A fire retardant agent having the general formula (1)

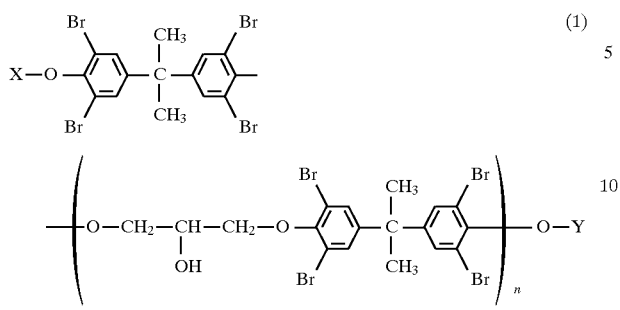

wherein

X and Y are independently selected from the group consisting of A and B shown in formula (2)

A: 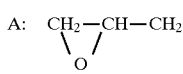 (2)

B: 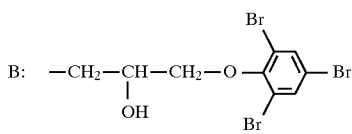

and n is the mean degree of polymerization and is from 0 to 30;

said fire retardant agent being a mixture including 15 to 30% of X=Y=A, 40 to 60% of X=A and Y=B and 20 to 35% of X=Y=B;

said fire retardant agent having been produced by a process selected from the group consisting of:
(i) reacting tetrabromo bisphenol A, tribromo phenol and epichlorohydrine in the presence of an alkali metal hydroxide,
(ii) reacting tetrabromo bisphenol A, tribromo phenyl glycidyl ether and epichlorohydrine in the presence of an alkali metal hydroxide,
(iii) reacting tetrabromo bisphenol A epoxy resin having an epoxy equivalent of 350 to 700 g/eq, a softening point of 50° to 105° C. and a bromine content of 46 to 52%, tetrabromo bisphenol A and tribromo phenol in the presence of a catalyst selected from the group consisting of a phosphine and a phosphonium compound,
(iv) reacting tetrabromo bisphenol A epoxy resin having an epoxy equivalent of 600 to 1300 g/eq, a softening point of 95° to 140° C. and a bromine phenol in the presence of a catalyst selected from the group consisting of a phosphine and a phosphonium compound, and
(v) reacting tetrabromo bisphenol A epoxy resin having an epoxy equivalent of 350 to 700 g/eq, a softening point of 50° to 105° C. and a bromine content of 46 to 52%, tetrabromo bisphenol A and tribromo phenyl glycidyl ether in the presence of a catalyst selected from the group consisting of a phosphine and a phosphonium compound.

2. A flame-retarded thermoplastic resin composition including the fire-retardant agent of claim 1.

3. The process for producing fire retardant agent of claim 1, characterized by reacting tetrabromo bisphenol A, tribromo phenol and epichlorohydrine in the presence of alkali metal hydroxide.

4. The process for producing fire retardant agent of claim 1, characterized by reacting tetrabromo bisphenol A, tribromo phenyl glycidyl ether and epichlorohydrine in the presence of alkali metal hydroxide.

5. The process for producing fire retardant agent of claim 1, characterized by reacting tetrabromo bisphenol A epoxy resin having an epoxy equivalent of 350 to 700 g/eq, a softening point of 50° to 105° C. and a bromine content of 46 to 52%, tetrabromo bisphenol A and tribromo phenol in the presence of a catalyst selected from the group consisting of a phosphine and a phosphonium compound.

6. The process for producing fire retardant agent of claim 1, characterized by reacting tetrabromo bisphenol A epoxy resin having an epoxy equivalent of 600 to 1300 g/eq, a softening point of 95° to 140° C. and a bromine content of 50 to 53% and tribromo phenol in the presence of catalyst selected from the group consisting of a phosphine and a phosphonium compound.

7. The process for producing fire retardant agent of claim 1, characterized by reacting tetrabromo bisphenol A epoxy resin having an epoxy equivalent of 350 to 700 g/eq, a softening point of 50° to 105° C. and a bromine content of 46 to 52%, a tetrabromo bisphenol A and a tribromo phenyl glycidyl ether in the presence of a catalyst selected from the group consisting of a phosphine and a phosphonium compound.

8. The process for producing fire retardant agent as claimed in claim 5, 6 or 7, wherein the catalyst is a phosphonium compound catalyst.

* * * * *